United States Patent [19]

Sanderson et al.

[11] 4,012,286

[45] Mar. 15, 1977

[54] DETERMINATION OF CREATINE PHOSPHOKINASE IN BODY FLUIDS

[75] Inventors: James Allen Sanderson; William S. Stavropoulos, both of Indianapolis, Ind.

[73] Assignee: The Dow Chemical Company, Midland, Mich.

[22] Filed: Apr. 9, 1976

[21] Appl. No.: 675,389

[52] U.S. Cl. .......................... 195/103.5 R; 195/99
[51] Int. Cl.² ................. G01N 31/14; G01N 33/00
[58] Field of Search ............................ 195/103.5 R

[56] References Cited
UNITED STATES PATENTS 3,929,580  12/1975  Forgione et al. ........... 195/103.5 R

OTHER PUBLICATIONS

Warren "Activation of Serum Creative Kinase by Dithiothreitol" Clin. Chem. vol. 18, No. 5, 1972 pp. 473–475.

Primary Examiner—A. Louis Monacell
Assistant Examiner—C. A. Fan
Attorney, Agent, or Firm—James W. Ambrosius

[57] ABSTRACT

An improved method and compositions useful for determining the creatine phosphokinase activity of body fluids suitable for use on clinical colorimeters which involves pre-activation of the creatine phosphokinase with a novel pre-activation composition and comparison to a chemical standard.

6 Claims, 1 Drawing Figure

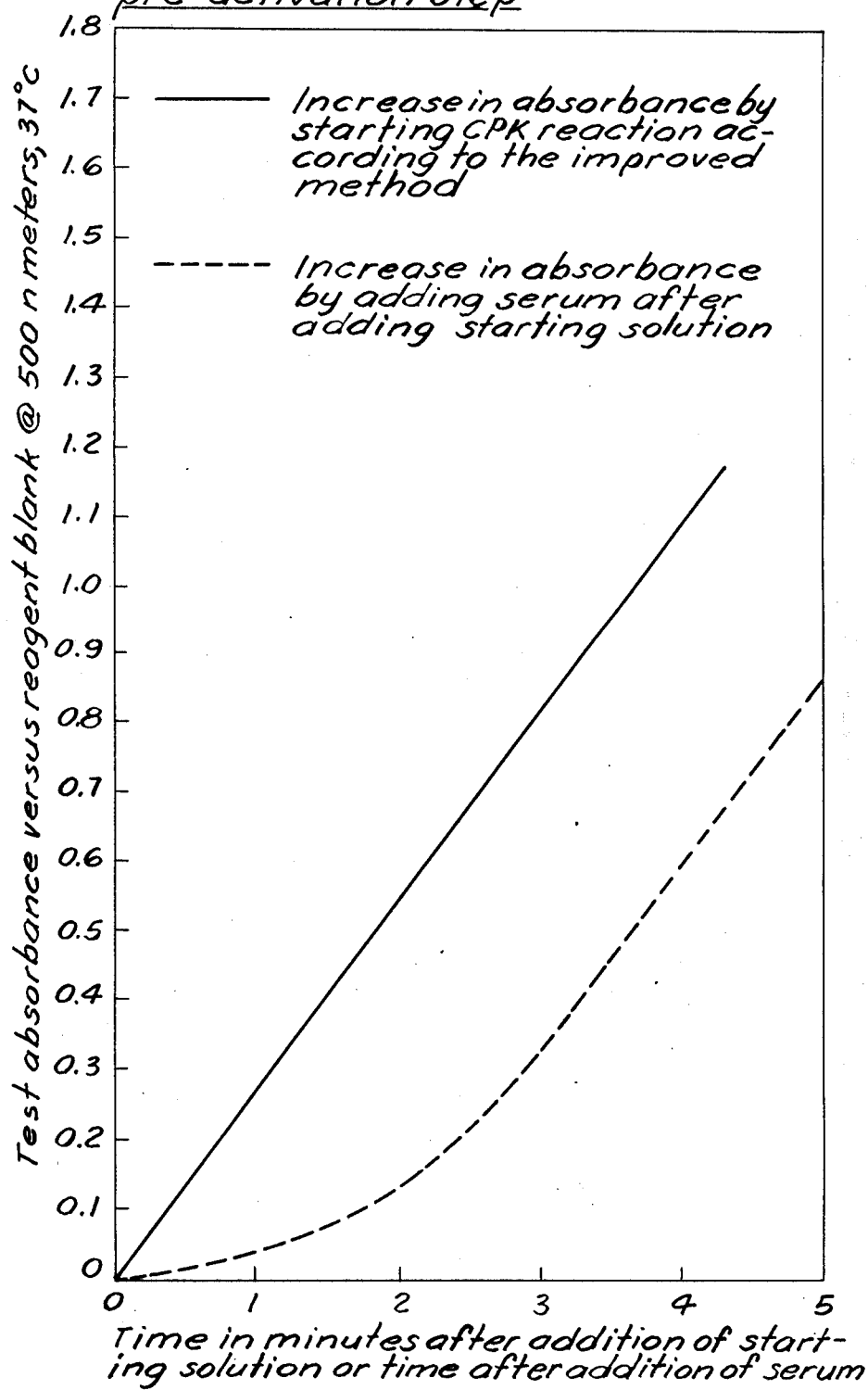

DETERMINATION OF CREATINE PHOSPHOKINASE IN BODY FLUIDS

BACKGROUND OF THE INVENTION

The enzyme creatine phosphokinase, hereafter abbreviated CPK, is found in normal human serum and catalyzes the transfer of phosphate from creatine phosphate to adenosine diphosphate (ADP) to form adenosine triphosphate (ATP) and creatine. Analysis of CPK concentration in the serum is commonly used in the diagnosis of human diseases or disorders such as myocardial infarction, pulmonary infarction, cerebral infarction, hypothyroidism, liver disorder, skeletal muscle damage due to trauma or injury, and muscular dystrophy.

An assay method for CPK using the reverse reaction of creatine phosphokinase and adenylate kinase was developed by Oliver, *Biochem J.* 61, 116(1955). This method was later improved by Rosalki, *J. Lab. Clin. Med.* 61, 696(1967), and Hess, et al., *Am. J. Clin. Path* 50, 89(1969). Further modifications of the procedure permitted the use of nicotinamide adenine dinucleotide (NAD) instead of nicotinamide adenine dinucleotide phosphate (NADP) in the final ultraviolet detection step. See Okinaka, et al., *J. Lab and Clinical Med.* 64, 299(1964). The key reactions may be summarized as follows:

I. oxidized inactive CPK + reduced thiol activator → reduced active CPK + oxidized thiol activator

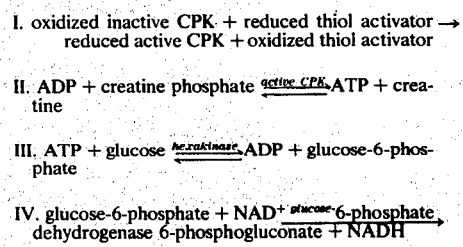

To eliminate the need for ultraviolet detecting instrumentation the NADH formed in reaction IV above may be converted to $NAD^+$ with the subsequent reduction of the tetrazolium compound 2-(p-iodophenyl)-3-(p-nitrophenyl)-5-phenyl tetrazolium chloride, hereafter INT, to form the red formazan dye INTH via enzymatic catalysis by diaphorase. See Avigad and Levin, *N, Europ. J. Biochem* 1, 102(1969). This reaction may be expressed as follows:

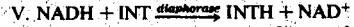

Hereinafter the sequence of reactions I through V will be called the Oliver-Rosalki-formazan method. A body fluid, such as serum, plasma, lymphatic fluid or the like is analyzed for CPK activity using this method by adding test fluid to a prewarmed reconstituted lypholized substrate containing activator, primary substrates, intermediate substrates, final substrates, coupling enzymes, adenylate kinase inhibitor AMP, buffering compounds and stabilizers. The test fluid is incubated (at about 37° C) for a fixed period of time (usually about 10 minutes) and then the reaction is stopped by the addition of acid. Likewise, water is added to another substrate and run as a reagent blank. Control serum having a known CPK activity is used to determine the activity of the unknown test serum.

The Oliver-Rosalki-formazan method as currently in use has four major drawbacks. First, there is variable lag time in the activation of CPK by the thiol activator in reaction I described above. While this lag can be followed using sophisticated continuously monitoring colorimetric measuring equipment having a reagent blank vial and using a double beam, this lag is a disadvantage when an end point method is used as employed in batch analysis. Thus if less sophisticated colorimetric equipment is used for end point method analysis some variation in results is unavoidable in the method as currently employed. Second, there is a continuous increase in the reagent blank absorbance following reconstitution of the substrate because of the presence of all the components necessary for non-serum CPK chromogen production. Third, there is a difference between the reagent blank vial's absorbance and the test vial's absorbance due to the variable degree of solubilization of the final chromogen, INTH, in the presence of serum. This results in an inadequate reagent blank. Fourth, the control serum is unstable and displays variable activation times which necessitates labelling commercial serum containing CPK with wide ranges of activity.

The present invention is directed to an improved Oliver-Rosalki-formazan method which overcomes the disadvantages of the current method. This improved method allows for accurate enzymatic measurement in end point analysis using standard clinical grade colorimeters.

DESCRIPTION OF DRAWING

The FIGURE is a demonstration of the improved Oliver-Rosalki-formazan method compared to the conventional method of carrying out the same reactions. The solid line shows chromogen development graphed against time using the improved method which incorporates a pre-activation step. The broken line shows the lag in chromogen development which occurs in the absence of pre-activation. The FIGURE is more fully discussed in Example 3 hereinafter.

SUMMARY OF THE INVENTION

The present invention relates to a unique method of carrying out the Oliver-Rosalki-formazan reaction sequence and to a unique composition for use in carrying out the reaction sequence. An objective of the present invention is to provide an accurate method for performing CPK enzyme analysis on a body fluid using an end point method which can be run on standard clinical grade colorimeters. Another objective of the present invention is to provide a CPK test method which incorporates an improved chemical standard which is less variable than the control serum currently in use.

The improved Oliver-Rosalki-formazan method that is the subject of the present invention differs from methods currently in use for CPK analysis in three important respects. (1) The serum CPK is pre-activated prior to the start of enzyme catalysis and chromogen production. (2) A surfactant has been added to the enzyme substrate to aid in the solubilization of the chromogen eliminating the positive solubilization of serum on INTH. (3) As a result of the improved chromogen solubilization in the absence of serum the control serum has been replaced by an intermediate reaction product, i.e., a pure chemical standard, which is subsequently converted to the final chromogen.

Pre-activation of the inactive CPK is accomplished by a reduced thiol activator such as for example, glutathione, dithiothreitol, N-acetyl cysteine, or cysteine (Reaction I above) prior to the beginning of enzyme catalysis and chromogen production. Sufficient thiol activator must be present to activate all of the CPK present in the body fluid. Therefore an excess of thiol activator is generally employed to assure the total activation of all CPK present. The CPK-activating amount of the thiol activator may be determined by the simple expedient of measuring the intensity of color produced with varying amounts of added activator when samples having known concentrations of CPK are employed. Pre-activation eliminates the inaccuracy resulting from the variable activation time of serum CPK because the CPK is fully active before coming into contact with the primary substrate ADP. This has been found to linearize chromogen production once the enzymatic reaction begins.

Side reactions which result in non-serum CPK chromogen production are also minimized by pre-activation of the CPK in the absence of the final intermediate substrates INT and ADP. Three chromogen contributing side reactions which can lead to inaccurate results are (a) the reduction of INT by the thiol activator rather than by NADH, (b) the catalysis of ADP by CPK present as a contaminant in the coupling enzymes glucose-6-phosphate dehydrogenase and hexokinase, and (c) the fact that the inhibitor AMP of adenylate kinase does not completely eliminate adenylate kinase interference found in the coupling enzymes of (b) above. By eliminating both ADP and INT from the pre-activation mixture these side reactions are unable to take place prior to the beginning of the CPK enzymatic reaction.

The improved Oliver-Rosalki-formazan method therefore incorporates a unique sequence of steps in the carrying out of this method. In summary these steps are:

1. Preactivation step — The serum is mixed with a partial substrate containing a thiol activator, preferably glutathione, primary substrates, intermediate substrates, coupling enzymes, buffering compounds and stabilizers. However, missing from the partial substrate are the primary substrate ADP and the final substrate INT. The inhibitor AMP may also be added later, however, preferably it is added after the pre-activation step. The pre-activation mixture is incubated, typically in a water bath or heating block at a temperature of from about 25° to about 40° C, 30° to 37° C being preferred, for a length of time sufficient to optimally activate the CPK, generally about 8 to 10 minutes. In the preparation of the materials for the preactivation step it is preferred to employ two separate compositions, a first lypholyzed partial substrate composition containing activator, creatine phosphate, NAD, glucose, hexokinase, glucose-6-phosphate dehydrogenase, and diaphorase and a second reconstituting reagent containing a buffer with a pH of between 6 and 7 and surfactant. When the ingredients for the partial substrate are thus prepared as two separate compositions, both such compositions are stable for long periods of time prior to use. The separate compositions are mixed to provide the reconstituted partial substrate used in the pre-activation step.

2. Enzyme catalysis step — A starting reagent, containing the primary substrate ADP, a tetrazolium salt dye such as INT, and the inhibitor AMP is mixed with the incubated pre-activation mixture.

3. Addition of stop reagent — a major advantage of the improved method is that it may be used to accurately measure CPK activity on clinical grade colorimeters. Usually this will require that the chromogen producing reaction be stopped by the addition of acid, as for instance hydrochloric acid (HCl), after a time sufficient to allow adequate chromogen development. Ten minutes has been found to give satisfactory chromogen development.

The above reactions take place generally at a pH of between 6 and 7 with a pH of from 6.3 to 6.5 being preferred.

In addition, to the unique sequence of steps employed in the improved Oliver-Rosalki-formazan method, an INTH solubilizing amount of a surfactant has been added to aid in the solubilization of INTH. While surfactants have been used in the past none of them have been entirely satisfactory for the purpose, and the insolubility of INTH in the presence of serum and more importantly the difference in solubility in the presence and in the absence of serum has remained a problem. The present invention uses the polyoxyethylated vegetable oil Emulphor EL620 (GAF Corp.) at a concentration of between 0.02 and 0.10% weight/volume with a concentration of about 0.025% weight/volume being preferred.

Emulphor EL260 (GAF Corp.) is described as an essentially anhydrous (0.5% max. water content) polyoxyethylated vegetable oil having a viscosity of 600–1,000 cps at 25° C, a specific gravity of 1.04–1.05 at 25° C, and a density of 8.7–8.8 lb/gal at 25° C. It is a nonionic ether-ester type surfactant which is soluble in water, acetone, carbon tetrachloride, ethanol, vegetable oil, ether, toluene, xylene, and methanol. It is partially soluble in mineral oil and is insoluble in mineral spirits and ethylene glycol. Emulphor EL620 is stable in the presence of metallic ions and weak alkali, but is only partially stable in 1% acid. The lime-soap dispersion index is 5% and the neutralization number is 0.5 maximum (mg KOH/g sample to pH 7.0). The surface properties are shown in Table I below.

TABLE I

| Concd. in distd. water at 25° C(%) | 0.001 | 0.01 | 0.1 |
|---|---|---|---|
| Surface Tension (dynes/cm) | 52 | 42 | 41 |
| Interfacial Tension (dynes/cm) | 22 | 13 | 10 |
| Spreading Coefficient (ergs/cm$^2$) | 44 | 26 | 20 |

Other polyoxyethylated vegetable oils having the chemical structure and physical characteristics of Emulphor EL260 could be used to solubilize the tetrazolium salt dye.

The superiority of the surfactants such as those disclosed above over surfactants used in the prior art is such that a chemical standard may be used in place of the control serum standard used in other Oliver-Rosalki-formazan method. The chemical standard is superior to the serum standard because it is not subject to the variable CPK activity inherent when control serum is used. The chemical standard thus gives more predictable and accurate results. The present invention uses the chemical standard glucose-6-phosphate but it will be appreciated by one skilled in the art that other intermediate substrates of the Oliver-Rosalki-formazan reactions also may be employed. Glucose-6-phosphate is preferred because the chromogen formed is spectrophotometrically the same as that formed in the CPK reaction sequence described above.

The improved Oliver-Rosalki-formazan method as disclosed above requires two unique compositions, the preactivation reagent and the starting reagent; not employed or suggested heretofore. In addition, the chemical standard, glucose-6-phosphate, and the stop reagent, HCl, are required.

Preferred compositions of the above are as follows.

EXAMPLE 1

| Preactivation Reagent (reconstituted*) | |
| --- | --- |
| Glutathione activator | 5 m mole/liter |
| Creatine phosphate (from yeast) | 34.5 m mole/liter |
| Glucose | 12 m mole/liter |
| Hexokinase (from yeast) | 5.5 U/test |
| Glucose-6-phosphate dehydrogenase (from Leuconostoc mesenteroides) | 2.24 U/test |
| Diaphorase (from Clostridium Kluyoeri) | 3 U/test |
| Magnesium acetate | 14.4 m mole/liter |
| 3-(N-morpholino)propane sulfonic acid buffer | 82.18 m mole/liter |
| Surfactant (Emulphor EL 620) | 0.025% W/V |
| Nicotinamide adenine dinucleotide (yeast) | 2.77 m mole/liter |

*The proportions above represent the composition in the reconstituted state. In a preferred embodiment of the lypholyzed composition the sulfonic acid buffer and the surfactant would be absent and added later during reconstitution.

| Starting Reagent | |
| --- | --- |
| Adenosine-5'-diphosphate (from yeast) | 16.03 m mole/liter |
| Adenosine-5'-monophosphate (from yeast) | 42.07 m mole/liter |
| 2-(p-iodophenyl)-3-(p-nitrophenyl)-5-phenyltetrazolium chloride | 4.91 m mole/liter |

EXAMPLE 2

A preferred embodiment of the improved Oliver-Rosalki-formazan method is carried out as follows:

a. Transfer 1.0 ml of the preactivation reagent of Example 1 into each of 3 empty vials appropriately marked patient, blank, and standard.

b. Mix 0.05 ml of the patient's serum into the patient's vial and 0.05 ml of distilled water into the blank vial.

c. Incubate all three vials with about 0.66 ml of the starting reagent in a separate container in a 37° C heat source for about 8 to 10 minutes.

d. Mix 0.2 ml of the pre-warmed starting reagent into all three vials and continue incubation.

e. Add 0.05 ml of the chemical standard (glucose-6-phosphate 2 m moles/liter) to the standard vial.

f. Ten minutes after the addition of the starting reagent add 4.0 ml of the stopping reagent (hydrochloric acid 40 m mole/liter containing 0.6% w/v Emulphor EL 620 to each vial.

g. Using a colorimeter or spectrophotometer set at 500 nm run an analysis of the material. The indicating device on the colorimeter should have been previously set to read zero absorbance for distilled water. The absorbance of each of the three vials is read on the colorimeter and recorded.

The preferred way of expressing enzyme concentration is in International Units/liter (U/liter). One International Unit is the amount of enzyme that will transform one micromole of substrate per minute under standard conditions. Therefore the concentration of CPK in the patient's sample may be calculated using the following formula.

$$U/liter = \frac{A \text{ (Patient's vial)} - A \text{ (Blank vial)}}{A \text{ (Standards vial)} - A \text{ (Blank vial)}} \times \text{Conc. of standard in U/liter}$$

wherein A = absorbance.

A chemical standard using glucose-6-phosphate in a concentration of 2 m moles/liter which is equivalent to 200 U/liter of serum has been found satisfactory as a standard in the above procedure. Therefore in the above formula the value 200 U/liter would be used as the concentration of standard in U/liter.

EXAMPLE 3

The importance of the preactivation step in minimizing the variation of analysis results is demonstrated by comparing chromogen formation as indicated by increase in absorbance using the method outlined in Example 2 above to chromogen formation where no preactivation step is employed.

Using the operating procedure of Example 2 above, the increase in absorbance (indicating increasing enzyme catalyzed chromogen formation) was monitored continuously using a Varian model 635 Spectrophotometer set at 500 nanometers using a reagent blank, i.e., water in place of serum, in the reference cuvette.

The procedure above was repeated except water for the reagent blank and serum for the test were added after the addition of prewarmed starting solution to the prewarmed preactivation reagent. The results are presented graphically in the Figure.

The salient features to note in the FIGURE are as follows:

a. By preactivating the serum by the present unique improved methodology the reaction is linear within the measuring capacity of instrument from the beginning of the addition of the ADP substrate.

b. Without preactivation the Oliver-Rosalki-formazan method shows a pronounced lag of about 3 minutes prior to achieving linear production of the chromogen.

c. Since the methodology normally uses an endpoint (i.e., the reaction is stopped 10 minutes after the total reactants are combined) the improved method results in enhanced color development.

EXAMPLE 4

As noted above serum has a solubilizing effect upon the chromogen INTH. In the absence of the surfactant Emulphor EL 620 from the reaction mixture there is a positive bias that may be demonstrated by using a reagent blank employing heat treated serum (i.e., containing serum irreversibly inactivated CPK). To demonstrate this bias the following were prepared for analysis:

a. active serum assayed as 358 U/l.

b. heat treated serum (heat treated at 55° C for 2 hours c. water for use as a blank d. chemical standard (2 m M glucose-6-phosphate)

e. chemical standard mixed with heat treated serum.

Each of the materials listed above were assayed twice using the procedure outlined in Example 2 above. The assay methods used were identical except in one assay the surfactant Emulphor EL 620 was present in the reaction mixture and in the other assay the surfactant was absent. The results are compared in Table II.

TABLE II

| Material Assayed | Surfactant Present | | | Surfactant Absent | |
|---|---|---|---|---|---|
| | Activity U/l* | Reading** | Reading Minus Reagent Blank | Reagent Reading** | Reading Minus Blank |
| Reagent Blank (H₂O) | — | 0.153 | — | 0.026 | — |
| Active Serum | 3.58 | 0.951 | 0.798 | 0.789 | 0.763 |
| Heat treated Serum | less than 3 | 0.158 | 0.005 | 0.143 | 0.117 |
| Chemical Standard | 200 | 0.598 | 0.445 | 0.255 | 0.229 |
| Standard plus H.T. Serum | 200 | 0.594 | 0.441 | 0.494 | 0.468 |

*U/l = international units/liter
**Absorbance readings made on a DOW Enzyme Spectrophotometer set at 500 nanometers with an effective path length of 1.1 cm.

The results indicate that in the system containing the surfactant Emulphor EL 620 the absorbance of the reagent blank is independent of the presence of serum. The same is true of the chemical standard. The presence of serum does not change the readings appreciably when heat treated serum is present in the chemical standard. In the absence of surfactant the presence of serum dramatically increases the standard absorbance in the absence of the surfactant. The INTH produced by the glucose-6-phosphate in the chemical standard has failed to completely solubilize and has contributed to the variability seen when the readings for the chemical standard are compared to those for the chemical standard plus heat treated serum. This variation is not apparent in the system when the surfactant is present.

I claim:

1. An improved method for the determination of creatine phosphokinase in a body fluid wherein the body fluid is incubated with a mixture containing a thiol activator, creatine phosphate, hexokinase, glucose-6-phosphate dehydrogenase, glucose, nicotinamide adenine dinucleotide, adenosine-5'-diphosphate and a tetrazolium salt dye until a measurable color develops and the color is measured wherein the improvement comprises:
   a. incubating the body fluid with the thiol activator, creatine phosphate, hexokinase, glucose-6-phosphate dehydrogenase, glucose, nicotinamide adenine dinucleotide, and from 0.02 to 0.10% weight/volume of a nonionic ether-ester polyoxyethylated vegetable oil surfactant for a time sufficient to activate the creatine phosphokinase;
   b. mixing the resulting incubate with adenosine-5'-diphosphate, the tetrazolium salt dye, and adenosine-5'-monophosphate;
   c. incubating the resulting mixture for a time sufficient to develop measurable color; and
   d. stopping the reaction after a pre-determined time with an acid.

2. The method of claim 1 wherein the thiol activator is glutathione and the dye is 2-(p-iodophenyl)-3-(p-nitrophenyl)-5-phenyltetrazolium chloride.

3. The method of claim 2 wherein a chemical standard is prepared using glucose-6-phosphate.

4. The method of claim 2 wherein the body fluid is blood serum.

5. A kit for the determination of creatine phosphokinase comprising a first pre-activation composition having a thiol activator, creatine phosphate, hexokinase, glucose-6-phosphate dehydrogenase, glucose, nicotinamide adenine dinucleotide, and from 0.02 to 0.10% weight/-volume of a nonionic ether-ester polyoxytheylated vegetable oil surfactant and a second composition having adenosine-5'-diphoshate, adenosine-5'-monophosphate, and a tetrazolium salt dye.

6. The kit of claim 5 wherein the thiol activator is glutathione and the dye is 2-(p-iodophenyl)-3-(p-nitrophenyl)-5-phenyltetrazolium chloride.

* * * * *

UNITED STATES PATENT OFFICE
CERTIFICATE OF CORRECTION

Patent No. 4,012,286  Dated March 15, 1977

Inventor(s) James Allen Sanderson et al.

It is certified that error appears in the above-identified patent and that said Letters Patent are hereby corrected as shown below:

Title page, right column, title of Other Publication, "Activation of Serum Creative Kinase by Dithiothreitol" should read -- Activation of Serum Creatine Kinase by Dithiothreitol --.

Column 2, line 12, at the end of the line, "chor-" should read -- chro- --.

Column 4, line 53, "surfactants" should read -- surfactant --.

Column 4, lines 24 and 51, "Emulphor EL260" should read -- Emulphor EL620 --.

Column 6, line 1, "wherein A = absorbance." should be deleted; it is a repetition of the last line of Column 5.

Column 7, TABLE II, last two sub-titles to the right, "Reagent Reading" and "Reading Minus Blank" should be -- Reading -- and -- Reading Minus Reagent Blank --.

Column 7, TABLE II, Column titled Activity U/l*, "3.58" should read -- 358 --.

UNITED STATES PATENT OFFICE
CERTIFICATE OF CORRECTION

Patent No. 4,012,286  Dated March 15, 1977

Inventor(s) James Allen Sanderson et al,

It is certified that error appears in the above-identified patent and that said Letters Patent are hereby corrected as shown below:

Column 8, line 43, "theylated" should read -- ethylated --.

Column 8, line 44, "adenosine-5'-diphoshate," should read -- adenosine-5'-diphosphate, --.

Signed and Sealed this second Day of August 1977

[SEAL]

Attest:

RUTH C. MASON
Attesting Officer

C. MARSHALL DANN
Commissioner of Patents and Trademarks